US005288882A

United States Patent [19]
Shih et al.

[11] Patent Number: 5,288,882
[45] Date of Patent: Feb. 22, 1994

[54] PROCESS FOR RECOVERING AN OPTICALLY ACTIVE EPOXY ALCOHOL

[75] Inventors: T. Thomas Shih, Bryn Mawr; Wilfred P.-S. Shum, West Chester, both of Pa.

[73] Assignee: Arco Chemical Technology, L.P., Wilmington, Del.

[21] Appl. No.: 994,030

[22] Filed: Dec. 21, 1992

[51] Int. Cl.$^5$ ............... C07D 301/32; C07D 303/14; C07D 303/16
[52] U.S. Cl. ................... 549/541; 549/513; 549/556
[58] Field of Search .............. 549/541, 513, 556

[56] References Cited

U.S. PATENT DOCUMENTS

| | | | |
|---|---|---|---|
| 3,374,153 | 3/1968 | Naglieri | 203/44 |
| 3,655,524 | 4/1972 | Mednick | 203/67 |
| 3,920,708 | 11/1975 | Kubo et al. | 260/348.5 L |
| 4,009,188 | 2/1977 | Heim et al. | 260/348.5 L |
| 4,082,777 | 4/1978 | Fisher et al. | 260/348.25 |
| 4,471,130 | 9/1984 | Katsuki et al. | 549/523 |
| 4,594,439 | 6/1986 | Katsuki et al. | 549/523 |
| 4,764,628 | 8/1988 | Shum | 549/529 |
| 4,900,847 | 2/1990 | Hanson et al. | 549/529 |
| 4,935,451 | 6/1990 | Dittmer et al. | 549/556 |
| 4,946,974 | 8/1990 | Sharpless et al. | 549/556 |
| 5,041,559 | 8/1991 | Sato | 549/215 |

FOREIGN PATENT DOCUMENTS

| | | |
|---|---|---|
| 61-10571 | 1/1986 | Japan . |
| 12680 | 1/1986 | Japan ............... 549/541 |
| 61-12680 | 1/1986 | Japan . |

OTHER PUBLICATIONS

Bobyler et al., *Massoobmennye Teploobmennye Protsessy Khim*, Teknol. pp. 108–114 (1977).
Pfenninger, *Synthesis* pp. 89–116 (1986).
Gao et al., *J. Am. Chem. Soc.* 109, 5765–5780 (1987).
Katsuki et al., *J. Am. Chem. Soc.* 102, 5974–5976 (1980).
Finn et al., in *Asymmetric Synthesis*, Morrison, ed., Academic Press, New York (1985), vol. 5, Chapter 7, pp. 193–246.
Rossiter in *Asymmetric Synthesis*, Morrison, ed. Academic Press, New York (1985), vol. 5, Chapter 7, pp. 193–246.

*Primary Examiner*—Joseph E. Evans
*Attorney, Agent, or Firm*—Stephen D. Harper

[57] ABSTRACT

A method of recovering optically active epoxy alcohols from asymmetric epoxidation reaction mixture is provided whereby the epoxy alcohol may be obtained in high yield with minimal degradation of optical purity. The process is also suitable for the synthesis of useful organic sulfonate derivatives of chiral epoxy alcohols.

21 Claims, No Drawings

PROCESS FOR RECOVERING AN OPTICALLY ACTIVE EPOXY ALCOHOL

FIELD OF THE INVENTION

This invention pertains to methods for recovering optically active glycidol and related 2,3-epoxy alcohols in purified form from asymmetric epoxidation reaction mixtures.

BACKGROUND OF THE INVENTION

Optically active (non-racemic) epoxy alcohols such as (R)- and (S)- glycidol are extremely useful and versatile starting materials and intermediates in the synthesis of chiral natural products and natural product analogues or derivatives. Many such optically active products derived from chiral epoxy alcohols have a high physiological activity and thus are of great interest in the pharmaceutical field. The synthetic utility of non-racemic epoxy alcohols has been extensively reviewed in Hanson, *Chemical Reviews* 91(4), 437–473 (1991).

Recently, the preparation of optically active epoxy alcohols from inexpensive racemic starting materials such as allylic alcohols has become feasible on a commercial scale due to the development of an asymmetric epoxidation method by Dr. K. Barry Sharpless and co-workers wherein an allylic alcohol is reacted with an organic hydroperoxide in the presence of a titanium/chiral carbinol complex catalyst. While this method affords good yields of epoxy alcohol having high optical purity, recovery of the epoxy alcohol from the crude epoxidation reaction mixture is not simple due to the number of different substances present (typically, epoxy alcohol, unreacted allylic alcohol, unreacted hydroperoxide, organic solvent, the alcohol derived from reduction of the hydroperoxide during epoxidation, and catalyst are all present). In addition, glycidol and related compounds are notoriously unstable and reactive. Significant losses due to polymerization, ring-opening (e.g., hydrolysis or alcoholysis), acid-catalyzed or thermal decomposition, and the like are often encountered during purification of these substances.

The development of improved methods whereby optically active glycidol or the like may be isolated from an asymmetric epoxidation reaction mixture in high yield with minimal loss of optical purity would therefore be of considerable value.

SUMMARY OF THE INVENTION

This invention provides a process for recovering an optically active epoxy alcohol from an asymmetric epoxidation reaction mixture comprised of the optically active epoxy alcohol, an organic hydroperoxide, and a transition metal chiral ligand complex epoxidation catalyst, said process comprising the steps of (a) contacting the asymmetric epoxidation reaction mixture with
 (i) a reducing agent selected from sulfur (II) compounds, sulfur (III) compounds and phosphorous (III) compounds, in an amount effective to reduce the organic hydroperoxide;
 (ii) a polyalcohol, in an amount effective to inhibit the epoxidation catalyst; or
 (iii) both said reducing agent and said polyalcohol;

(b) conducting a distillation in the presence of an azeotropic agent forming a minimum boiling heterogeneous azeotrope with the epoxy alcohol selected from aromatic hydrocarbons, halogenated aliphatic hydrocarbons, and aliphatic hydrocarbons to remove in vapor form an overhead product comprised of the optically active epoxy alcohol and the azeotropic agent;

(c) condensing the overhead product in liquid form whereby the condensed overhead product phase-separates to form an epoxy alcohol-rich phase and an epoxy alcohol-lean phase; and (d) separating the epoxy alcohol-rich phase from the epoxy alcohol-lean phase.

DETAILED DESCRIPTION OF THE INVENTION

Optically active epoxy alcohols which may be recovered using the process of this invention include the class of organic compounds containing both a hydroxyl group and an epoxide (oxirane) group as well as a chiral center. The instant process is particularly useful for the purification of epoxy alcohols which are liquids at room temperature and relatively low boiling (e.g., less than about 250° C. at atmospheric pressure) since such substances cannot be readily isolated by conventional methods such as crystallization. Illustrative optically active epoxy alcohols include those compounds corresponding to the general structure

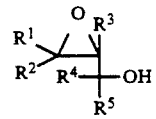

wherein $R^1$, $R^2$, $R^3$, $R^4$, and $R^5$ are the same or different and are selected from hydrogen, alkyl, aryl, and aryl alkyl, preferably hydrogen, $C_1$–$C_6$ alkyl, $C_6$–$C_{10}$ aryl, and $C_7$–$C_{10}$ aryl alkyl. Preferably, either all of the R substituents are hydrogen or only one of $R^1$, $R^2$, $R^3$, $R^4$, and $R^5$ is a substituent other than hydrogen, with the remaining substituents all being hydrogen. The non-hydrogen substituent in this preferred embodiment is most preferably a $C_1$–$C_6$ alkyl group such as methyl, ethyl, n-propyl, iso-propyl, n-butyl, sec-butyl, tert-butyl, isobutyl, n-hexyl, cyclohexyl and the like. Specific preferred epoxy alcohols include the optical isomers (R or S) of glycidol (also known as oxirane methanol), 2-methyl glycidol (2-methyl oxirane methanol), 3-methyl glycidol (3-methyl oxirane methanol), and the like.

The asymmetric epoxidation reaction mixture to be processed in accordance with the present invention may be obtained by any of the conventional techniques known in the art for generating such a mixture. Such techniques are described in detail in the following publications, all of which are incorporated herein by reference in their entirety: Sheldon, *Aspects Homogeneous Catal.* 4, 3(1981); Jorgensen, *Chem. Dev.* 89, 431(1989); U.S. Pat. No. 4,471,130 (Katsuki et al.); U.S. Pat. No. 4,764,628 (Shum); U.S. Pat. No. 4,594,439 (Katsuki et al.); European Pat. Pub. No. 197,766; European Pat. Pub. No. 70,618; European Pat. Pub. No. 255,379; Pfenninger, *Synthesis* 89(1986); Gav et al. *J. Am. Chem. Soc.* 109, 5765(1987); Katsuki et al., *J. Am. Chem. Soc.* 102, 5974(1980); Finn et al. in *Asymmetric Synthesis*, Morrison, ed., Academic Press, New York(1985), Vol. 5, Chapter 8, p.247; Rossiter in *Asymmetric Synthesis*, Morrison, ed., Academic Press, New York(1985), Vol. 5, Chapter 7, p.193. Such methods involve the reaction of an organic hydroperoxide with an allylic alcohol in the presence of a transition metal catalyst having a chiral ligand complexed with the metal and an organic solvent. The organic hydroperoxide is typically a secondary or tertiary aliphatic or aromatic hydroperoxide such as t-butyl hydroperoxide, t-amyl hydroperoxide, cumene hydroperoxide, ethyl benzene hydroperoxide, cyclohexyl hydroperoxide, triphenylmethyl hydroperoxide, and the like. The allylic alcohol is selected such that it will yield the desired optically active epoxy alcohol upon epoxidation and thus may be allyl alcohol, methallyl alcohol (2-methyl-2-propen-1-ol), 3-buten-1-ol, and the like. The transition metal in the catalyst is preferably selected from titanium, molybdenum, zirconium, vanadium, tantulum, and tungsten, with titanium having preferred due to its relatively high activity and stereoselectivity when complexed with a chiral ligand. Suitable chiral ligands are described in detail in the publications cited hereinabove. A particularly preferred class of chiral ligands, however, are chiral carbinols such chiral (asymmetric) glycols (dihydroxy compounds) such as ester and amide derivatives of tartaric acid. The organic solvent is selected so as to provide rapid and stereoselective conversion of allylic alcohol to the optically active epoxy alcohol. Especially preferred solvents for use include halogenated hydrocarbons such as methylene chloride, dichloroethane, carbon tetrachloride, and the like, aliphatic hydrocarbons such as hexane, isooctane, cyclohexane, and the like, as well as aromatic hydrocarbons such as toluene, ethyl benzene, and cumene.

The relative proportions of each of the components present in the asymmetric epoxidation reaction mixture will, of course, vary considerably depending upon the initial ratios and concentrations of reactants, the reactivity and chemical structure of each component, and the extent to which conversion of the allylic alcohol is carried out prior to the start of epoxy alcohol recovery, but typical ranges and proportions are as follows:

|   | wt % |
|---|---|
| epoxy alcohol | 1–30 |
| unreacted allylic alcohol | 0.05–10 |
| unreacted hydroperoxide | 0.05–30 |
| alcohol derived from hydroperoxide | 1–30 |
| catalyst | 0.1–5 |
| solvent | 30–80 |

The asymmetric epoxidation reaction mixture is contacted with one or more treating agents so as to effectively accomplish either inhibition of the epoxidation catalyst and/or reduction of the organic hydroperoxide. The asymmetric epoxidation is desirably conducted using a significant stoichiometric excess of hydroperoxide relative to the allylic alcohol being epoxidized in order to attain the highest possible optical purity. It is important to render the resulting reaction product mixture essentially free of active oxygen since the subsequent azeotropic distillation step should be accomplished in the absence of hydroperoxide so as to avoid the safety hazards associated with concentration or distillation of such unstable substances and to avoid any undesired by-products arising from the reaction of hydroperoxide. In particular, we have found that if the excess hydroperoxide is left in the mixture during distillation, additional epoxidation of the unreacted allylic alcohol takes place. However, this additional epoxidation is much less stereoselective than the epoxidation which took place initially due to the higher reaction temperatures encountered during distillation. The overall optical purity of the epoxy alcohol product is thereby adversely affected. In addition, the excess hydroperoxide may ring-open the epoxy alcohol to form impurities. These detrimental effects may be avoided by contacting the asymmetric epoxidation reaction mixture with an amount of an appropriate reducing agent selected from sulfur (II) compounds, sulfur (III) compounds, and phosphorous (III) compounds sufficient to substantially or, more preferably, to completely reduce the hydroperoxide to the corresponding alcohol. Reducing agents of this type have been found to be particularly effective for this purpose since the desired reduction proceeds cleanly with minimal by-product formation or release of oxygen gas as can occur in other hydroperoxide decomposition reactions. These reducing agents also exhibit surprisingly little tendency to interact adversely with the optically active epoxy alcohol which, as discussed hereinabove, is extraordinarily susceptible to degradation. Normally, it will be advantageous to utilize a slight excess of the reducing agent relative to the number of equivalents of hydroperoxide present (e.g., from about 1 to 30 percent stoichiometric excess) in order to assure complete hydroperoxide reduction. Illustrative sulfur (II) and sulfur (III) compounds appropriate for use include both organic and inorganic species wherein the sulfur is present in an oxidation state of II or III such as, for example, alkali metal salts of hydrogen sulfites ($HSO_3M$), sulfites ($SO_3M_2$), and disulfites ($HS_2O_3M$ and $M_2S_2O_5$) and the like such as sodium bisulfite ($NaHSO_3$), sodium metabisulfite ($Na_2S_2O_5$), potassium bisulfite ($KHSO_3$), potassium metabisulfite($K_2S_2O_5$), potassium sulfite ($K_2SO_3$), sodium sulfite ($Na_2SO_3$), sodium hydrosulfite ($Na_2S_2O_4$), lithium sulfite ($Li_2SO_3$), the corresponding alkaline earth salts of hydrogen sulfites, sulfites, and disulfites such as calcium sulfite ($CaSO_3$), calcium dihydrogen sulfite [$Ca(HSO_3)_2$], magnesium sulfite ($MgSO_3$), organic sulfides including compounds having the general structure $RSR^1$ wherein R and $R^1$ are the same or different and are an alkyl, aryl, or aryl alkyl group such as diphenyl sulfide, ethyl phenyl sulfide, benzyl phenyl sulfide, dibenzyl sulfide, diethyl sulfide and the like, and organic sulfoxides including compounds having the general structure $RSR^1$ wherein R and $R^1$ can have the same identities as described hereinabove for organic sulfides such as dibenzyl sulfoxide, dibutyl sulfoxide, dimethyl sulfoxide, 4,4'-ditolylsulfoxide and the like. Exemplary types of phosphorous (III) compounds suitable for use as the reducing agent in the process of this invention include organic phosphines such as those compounds having the general structure $RR^1R^2P$ wherein $R^1$, $R^2$, and $R^3$ are the same or different and are hydrocarbyl groups or substituted hydrocarbyl groups such as alkyl, aryl, and aryl alkyl (e.g., triphenyl phosphine, triethyl phosphine, diphenyl ethyl phosphine), organic phosphites (esters of phosphorous acid) such as those compounds having the general structure RO-$POR^2$ wherein R,$R^1$, and $R^2$ may be any of the groups described hereinabove (e.g., trimethyl phosphite, triisopropyl phosphite, triphenyl phosphite, tri(4-tolyl) phosphite), as well as inorganic or mixed organic-inorganic phosphorous(III) compounds such as sodium hypophosphite ($NaH_2PO_2$), sodium phenyl phosphinate, sodium phosphite ($Na_2HPO_3$), potassium hypophosphite, magnesium hypophosphite, calcium hypophosphite, and the like. The reducing agent should be selected such that it is neither highly acidic, since the decomposition of glycidol and other epoxy alcohols is accelerated by acidic substances, nor markedly nucleophilic, since an undesired ring-opening reaction with the epoxy alcohol may occur. Additionally, the choice of reducing agent will be made such that neither it nor the oxidized by-product therefrom interferes with the desired distillative recovery of the optically active epoxy alcohol.

To achieve the best yield of epoxy alcohol and to preserve the high optical purity of the epoxy alcohol product normally obtained at the conclusion of asymmetric epoxidation, the reaction mixture may alternatively or additionally be treated with a hydroxy group-containing catalyst inhibiting agent such as a polyalcohol so as to fully or completely deactivate the transition metal/chiral ligand complex catalyst. Without wishing to be bound by theory, it is thought that the polyalcohol functions as a catalyst inhibiting agent due to its ability to block the available reaction sites on the transition metal and inhibit further epoxidation or product decomposition. For this reason, polyhydroxy compounds such as glycols (1,2-diols), 1,3-diols, and the like which can form polydentate complexes with transition metals are especially preferred for use. Illustrative 1,2-diols include, for example, ethylene glycol, propylene glycol, catechol, 2,3-butanediol, and the like. The polyalcohol should be substantially non-acidic and non-reactive towards epoxy alcohol so as to maximize the yield of epoxy alcohol recovered by operation of the process of this invention. In addition, the boiling point of the polyalcohol should be such as to not compromise the purity of the epoxy alcohol recovered by operation of the process of this invention. Sufficient polyalcohol must be present so as to effectively inhibit the catalyst (i.e., to prevent it from causing loss of optical purity upon recovery of the chiral epoxy alcohol). In general, an amount of polyalcohol at least equivalent to the number of moles of transition metal in the epoxidation reaction mixture should preferably be added. A substantial excess may also be employed, however (e.g., up to a 50-fold molar excess relative to transition metal). We have surprisingly found that high yields of optically pure epoxy alcohol may be realized through the use of the polyalcohol inhibiting agent as described hereinabove even when the excess hydroperoxide is not reduced. Obviously, however, the appropriate safety precautions must be taken during distillation when this embodiment of the invention is utilized since the mixture will still contain the hydroperoxide.

While the temperature at which the polyalcohol and reducing agent are contacted with the asymmetric epoxidation reaction mixture prior to the azeotropic distillation step is not critical, temperatures of from −50° C. to 150° C. will typically be effective. The contact time may vary from 1 minute to 24 hours, depending upon the relative reactivities of the polyalcohol and/or reducing agent. Where the concentration of hydroperoxide is initially relatively high, it may be desirable to provide a means of removing heat from the asymmetric epoxidation reaction mixture and to add the reducing agent incrementally to avoid a runaway reaction. The reducing agent and polyalcohol may be added in neat liquid or powder form or, if desired, dissolved or slurried in a suitable solvent or carrier. If both a reducing agent and a polyalcohol catalyst inhibiting agent are utilized, they may be added sequentially in any order or as a mixture.

The asymmetric epoxidation reaction mixture is subsequently subjected to distillation in the presence of an azeotropic agent forming a minimum boiling heterogeneous azeotrope with the epoxy alcohol. The azeotropic agent is selected from aromatic hydrocarbons (preferably, $C_8$–$C_{12}$ aromatic hydrocarbons), halogenated aliphatic hydrocarbons (preferably, $C_2$–$C_{12}$ halogenated aliphatic hydrocarbons), and aliphatic hydrocarbons (preferably, $C_6$–$C_{15}$ aliphatic hydrocarbons). Illustrative aromatic hydrocarbons suitable for this purpose include cumene. Hexyl chloride and tetrachloroethylene are exemplary halogenated aliphatic hydrocarbons. Examples of appropriate aliphatic hydrocarbons include n-octane, n-heptane, isooctane, and ethyl cyclohexane. The azeotropic agent should be non-reactive towards the epoxy alcohol under the distillation conditions employed and should have a miscibility with the epoxy alcohol such that when the azeotrope comprised of azeotropic agent and epoxy alcohol is condensed from the vapor state and cooled (preferably, at a temperature of from −20° C. to 50° C.) the components of the azeotype separate into two distinct liquid phases. One phase is relatively rich in epoxy alcohol (typically, at least 80% by weight) whereas the other is relatively lean in epoxy alcohol (i.e., is comprised predominantly of the azeotropic agent). The amount of azeotropic agent utilized will be dependent upon the amount of epoxy alcohol to be removed by azeotropic distillation and the related proportion of each component in the azeotrope. As these factors are known or easily measured by standard methods, the minimum amount of azeotropic agent may thus be readily calculated. Sufficient azeotropic agent is present to azeotrope with all of the epoxy alcohol present in the initial mixture and suitably should be at least 1% in excess of this theoretical minimum requirement and preferably should be at least 5% in excess of this minimum. Where the azeotropic agent forms azeotropes with both the allylic alcohol and epoxy alcohol, the amount of azeotropic agent utilized should be sufficient to remove essentially all of these substances from the epoxidation reaction mixture.

The distillation may be carried out at atmospheric pressure or, especially where the epoxy alcohol/azeotropic agent azeotropic is relatively high boiling, at subatmospheric pressure (e.g., from about 0.1 up to 760 mm Hg). The pressure should be adjusted so as to provide an azeotrope boiling point (i.e., the temperature of the vapor taken overhead) between about 25° C. and 125° C. Preferably, the pot (bottoms) temperature does not at any point exceed 150° C., since epoxy alcohol decomposition and polymerization will thereby be minimized. When optically active glycidol is the epoxy alcohol being recovered, the distillation is most preferably performed at a pressure of from 1 to 100 mmHg so as to maintain a bottoms temperature of from 30° to 110° C. Conventional distillation columns of any configuration may be utilized, preferably columns having from 2 to 30 theoretical contacting stages operating with reflux ratios of from 1:1 to 15:1.

Any unreacted allylic alcohol which may be present in the asymmetric epoxidation reaction mixture may be first removed in vapor form as a first overhead product. This first overhead product may additionally comprise the azeotropic agent, depending upon whether the azeotropic agent and allylic alcohol form a minimum-boiling azeotrope. For example, cumene does not form an azeotrope with allkyl alcohol and thus the first overhead product would, where cumene is utilized as the azeotrope agent, contain allyl alcohol but not cumene.

Once all of the first overhead product (and thus all the allylic alcohol) has been removed, a second overhead product comprised of the optically active epoxy alcohol and the azeotropic agent (and which typically consists only of these components) is then removed and condensed in liquid form. The condensed second overhead product phase-separates to form an epoxy alcohol-rich phase (e.g., a phase comprising at least 70% by weight epoxy alcohol, more preferably at least 90% weight epoxy alcohol) and an epoxy alcohol-lean phase (e.g., a phase comprising no more than 30% by weight epoxy alcohol, more preferably no more than 10% weight epoxy alcohol).

For convenience, the azeotropic agent is selected such that it may also serve as the organic solvent during the asymmetric epoxidation reaction. The use of a different substance as the epoxidation solvent may, however, sometimes be desirable (so as to optimize optical purity, reaction rate, yield, etc.). In instances where the azeotrope (of epoxy alcohol and azeotropic agent) has a higher boiling point than the epoxidation solvent, the epoxidation solvent may first be removed from the epoxidation reaction mixture by an initial distillation (preferably, after addition of the azeotropic agent). Where the azeotrope has a lower boiling point than the epoxidation solvent, the epoxidation solvent may conveniently be left in the distillation bottoms and not taken overhead.

Once the second overhead product has sufficiently separated into two phases, the phases may be separated by any convenient technique such as decantation. The epoxy alcohol-rich phase will often be of sufficiently high purity that further purification is not necessary for most uses of the epoxy alcohol wherein the epoxy alcohol will be derivatized or reacted in some manner. For example, where R or S glycidol is the optically active epoxy alcohol and ethyl cyclohexane, n-octane, isooctane, or n-heptane is the azeotropic agent, the concentration of glycidol in the epoxy alcohol-rich phase will typically be from 95 to 98 weight percent. Certain other combinations of epoxy alcohols and azeotrope agents, however, may yield epoxy alcohol-rich phases having epoxy alcohol concentrations of less than 90 weight percent (for example, cumene yields a phase containing only about 82 weight percent glycidol).

If epoxy alcohol of higher purity is desired, the epoxy alcohol-rich phase after separation from the epoxy alcohol-lean phase may be redistilled such that an azeotrope comprised of the residual azeotropic agent and epoxy alcohol is vaporized and taken overhead. The azeotrope may be recycled. Essentially pure epoxy alcohol is often recoverable as a bottoms fraction from the redistillation in this manner. If high boiling impurities are present, it may be desirable to fractionally distill the epoxy alcohol away from such impurities.

Alternatively, the epoxy alcohol-rich phase comprised of epoxy alcohol and azeotropic agent may be utilized before or after separation from the epoxy alcohol-lean phase as a convenient source of epoxy alcohol in a derivatization reaction. The azeotropic agent will function as an inert solvent during such a derivatization so as to dissolve or disperse the epoxy alcohol derivative, reduce viscosity, or provide better temperature control. While the epoxy alcohol may be reacted in any known manner so as to form a derivative, the process of this invention is especially appropriate for the preparation of sulfonate derivatives of optically active epoxy alcohols. Such derivatives are of great interest as intermediates in the synthesis of beta blockers and other physiologically active compounds, as described in the following publications (all of which are incorporated herein by reference in their entirety): Klunder et al., *J. Org. Chem* 54, 1295–1304 (1989); Hanson, *Chemical Reviews* 91 (4), 453–456 (1991); U.S. Pat. No. 4,946,974 (Sharpless et al.); U.S. Pat. No. 5,153,338 (Sharpless et al.); U.S. Pat. No. 4,346,042 (Baldwin et al.); European Pat. Pub. No. 071,251; European Pat. Pub. No. 157,623; Gao et al., *J. Am. Chem. Soc.* 109; 5765 (1987); Pirrung et al., *Helv. Chem. Acta* 72, 1301–1310 (1998); Brunner et al., *Angew-Chem* 100 730–731 (1988); Shiratsuchi et al., *Chem. Pharm. Bull.* 35 3691–3698 (1987); PCT Int. Pat. Appl. WO 88-00,190; U.S. Pat. No. 4,877,892 (Brittelli); Jpn. Kokai 63-154,635; and Baldwin et al., *J. Med. Chem.* 25 931–936 (1982).

It has previously been suggested to carry out the derivatization of optically active epoxy alcohols with organic sulfonyl halides in situ immediately following an asymmetric epoxidation reaction. See, for example, Klunder et al., *J. Org. Chem.* 54, 1295–1304(1989). This derivatization method has the disadvantage, however, of providing relatively low isolated yields of the desired sulfonate derivatives when the stoichiometric ratio of epoxy alcohol:organic sulfonyl halide is approximately 1:1. Another drawback of this proposed synthetic scheme is that a number of tedious purification steps following the derivatization reaction are required. Without wishing to be bound by theory, we believe that these less than optimum yields are due, at least in part, to competing reactions of the organic sulfonyl halide with other protic species in the asymmetric epoxidation reaction mixture such as unreacted allylic alcohol and the alcohol derived from the organic hydroperoxide. In contrast, the process of this invention enables the recovery of sulfonate derivatives of optically active epoxy alcohols in high yield with minimum processing steps required.

In the process of this invention, the epoxy alcohol-rich phase may be contacted with an organic sulfonyl halide for a time and at a temperature effective to form the organic sulfonate derivative of the epoxy alcohol. Suitable organic sulfonyl halides include compounds having the general structure

wherein X is halogen (preferably, chlorine) and R is alkyl, aryl, or aryl alkyl. Illustrative R groups include alkyl groups such as methyl, ethyl, trifluoromethyl and t-butyl, aryl groups such as phenyl, 2-, 3-, or 4- tolyl, 3-nitro phenyl, 4-chlorophenyl, 3-nitro-4-chlorophenyl, 2,4,5-trichlorophenyl, 2-,3-, or 4-bromophenyl, 4-nitrophenyl, 2,4,6-triisopropyl phenyl, 4-methoxyphenyl, naphthyl, 2-nitrophenyl, 2,4-dinitrophenyl, 2-mesityl, cumenyl, and 2,5-dichlorophenyl, and aryl alkyl groups such as benzyl, phenethyl, and substituted derivatives thereof. The amount of organic sulfonyl halide should generally be approximately equal on a molar basis to the amount of optically active epoxy alcohol to be derivatized; molar ratios of from ca 1:0.7 to 0.7:1 organic sulfonyl halide: optically active epoxy alcohol will typically suffice. It may be desirable to have a tertiary amine such as triethyl amine or pyridine present during the derivatization to take up the hydrogen halide generated during the reaction and to minimize the acidity of the mixture. Temperatures of from ca. −40° C. to 100° C. (more preferably, −30° C. to 40° C.) will typically be sufficient to accomplish rapid derivatization with minimal epoxy alcohol decomposition or by-product formation. Once derivatization has proceeded to the desired extent, the organic sulfonate derivative of the optically active epoxy alcohol may either be taken on to subsequent synthesis steps (such as ring-opening with an appropriate nucleophile) without isolation or else recovered from the epoxy alcohol-rich phase by appropriate methods such as fractional distillation or crystallization.

The epoxy alcohol-lean phase may be recycled so as to recover the minor amount of epoxy alcohol contained therein and to reuse the azeotrope agent in subsequent azeotropic distillation cycles or batches.

In another embodiment of the process of this invention, highly pure organic sulfonate derivatives of the optically active epoxy alcohol may be conveniently obtained in high yield by contacting the asymmetric epoxidation reaction mixture with either a reducing agent and/or a polyalcohol and subsequently conducting a distillation in the presence of an aromatic hydrocarbon azeotropic agent forming a minimum boiling homogeneous azeotrope with the epoxy alcohol to remove in vapor form from the asymmetric epoxidation reaction mixture an overhead product comprised of the optically active epoxy alcohol and the azeotropic agent. The overhead product is condensed in liquid form so as to obtain a single phase condensate (preferably, at a temperature of from −20° C. to 75° C.). The condensed overhead product is contacted with an organic sulfonyl halide of the type described hereinabove for a time and at a temperature effective to form the desired organic sulfonate derivative of the epoxy alcohol. The organic sulfonate derivative may then be separated and recovered from the homogeneous azeotropic agent by any suitable means such as crystallization, extraction, distillation, or the like. Suitable aromatic hydrocarbon azeotropic agents include, but are not limited to, $C_6$–$C_{15}$ aromatic hydrocarbons such as toluene, ethylbenzene, o-xylene, chlorobenzene, and the like.

The azeotropic distillation step of this process can be carried out in a batch, step-wise; or continuous manner. The azeotropic agent can be added initially, in steps or continuously during distillation. The azeotropic agent can be introduced to the distillation in a mixture with the treated asymmetric epoxidation reaction mixture or separately therefrom.

Illustrative examples of heterogeneous azeotropic agents suitable for use in the process of this invention when the optically active epoxy alcohol is R- or S-glycidol are shown in Table I together with information regarding the boiling points and compositions of the azeotropes formed. Table II contains similar information related to the azeotropes obtained using illustrative homogeneous azeotropic agents suitable for use in this invention.

EXAMPLE 1

An asymmetric epoxidation of allyl alcohol was carried out in accordance with U.S. Pat. No. 4,900,847 using 32 g of allyl alcohol, 7.75 g of L(+)-diisopropyl tartrate, 15 g of activated 3A molecular sieves, 250 g of cumene, 7.75 g of titanium isopropoxide, and 208 g of 80% cumene hydroperoxide in cumene. After 14 hours at −15° C., the glycidol yield was determined by GC analysis to be 65%. The optical purity of the glycidol was found to be 88.5% e.e. (the S isomer predominating) by GC using a cyclodextrin-based capillary column.

The reaction mixture was combined with propylene glycol (21 g) to fully deactivate the titanium catalyst. The unreacted cumene hydroperoxide was then reduced to cumyl alcohol using 185 g tributyl phosphite. The reduction was carried out with good agitation at a temperature below −5° C. to minimize glycidol decomposition. After reduction was completed, the molecular sieves were removed by filtration prior to azeotropic distillation.

The reaction products obtained from a series of the foregoing epoxidation runs were distilled in a batch-wise manner using an Oldershaw distillation column one inch in diameter and having 20 perforated plates. Isopropanol (generated from the reaction of titanium isopropoxide with the diisopropyltartrate) and allyl alcohol were first distilled out at 10 Mm Hg pressure and a temperature of 45°–50° C. The glycidol was then taken overhead as an azeotropic mixture with cumene at 2–5 mm Hg pressure (overhead) and a reboiler temperature of 70° C. Residence time for the distillation run was 2–4 hours. The azeotrope condensate separated into two distinct phases upon cooling. The glycidol-rich phase containing about 80% glycidol was collected and analyzed by GC for chemical and optical purity. Overall glycidol recoveries were found to be in the range of 80–85%, with only 5–10% glycidol loss. The optical purity of the recovered glycidol remained at 88.5% e.e. When the propylene glycol was omitted prior to the azeotropic distillation, the optical purity was found to decrease slightly to 87.7–88.0% e.e.

EXAMPLE 2

The procedure of Example 1 was repeated, except that the epoxidation effluent was not treated with tributyl phosphite. The reboiler temperature was controlled below 75° C. and the distillate collected at an overhead pressure of 2–5 Mm Hg pressure. Residence time was typically 2–4 hours, with the distillations being carried out on a 300–500 g scale. Under these controlled conditions, cumene hydroperoxide decomposition was kept below 10%. When propylene glycol was added, the optical purity of the glycidol recovered decreased only slightly from 88.5% e.e. to 88.2% e.e. However, when no propylene glycol was present, the loss in optical purity of the glycidol was more pronounced (dropping from 88.5% e.e. to 87.2% e.e.). The deterioration in optical purity was attributed to the unsuppressed activity of the titanium tartrate catalyst, which catalyzes non-selective epoxidation of the remaining allyl alcohol with the excess unreduced cumene hydroperoxide present.

EXAMPLE 3

An asymmetric epoxidation was carried out using allyl alcohol (32 g), D(−)-diisopropyltartrate (7.75 g), activated 3A molecular sieves (15 g), titanium isopropoxide (7.75 g), and 80% cumene hydroperoxide in cumene (208 g). After 14 hours at −15° C., the yield of glycidol was found to be 65% based on GC analysis.

The reaction mixture was combined with tributylphosphite to reduce the unreacted cumene hydroperoxide to 2-phenyl-1-2-propanol. After removing the molecular sieves by filtration, the reaction mixture (608 g) was distilled using a 20 plate Oldershaw column at a reboiler temperature of 60°-68° C. and an overhead pressure of 3-5 mm Hg. The pressure drop per plate was ca. 1 mm Hg. Some distillate was also collected in a dry ice trap. The overall glycidol recovery was 84%, with only 3% remaining in the distillation pot as a bottoms fraction. Total glycidol loss during the 2.5 hour distillation was therefore only 13%. The optical purity of the (R)-glycidol recovered by distillation was 88.0% e.e.

To demonstrate that the heterogeneous distillate obtained as described hereinabove may be subsequently employed in the synthesis of aromatic sulfonate derivates of optically active glycidol, the distillate containing 84% (R)-glycidol in cumene was reacted with stoichiometric amounts of 3-nitrobenzene sulfonyl chloride and triethylamine to obtain optically pure (S)-glycidyl 3-nitrobenzene sulfonate as follows: 3-nitrobenzenesulfonyl chloride (10 g) was dissolved in toluene (100 g) and then combined with triethylamine (4.6 g). After cooling the solution to 5° C., the 84% (R)- glycidol distillate (3.96 g) was added. After 2 hours at 5° C. and 2 hours at 25° C., the reaction mixture was washed with water (100 g) to remove the triethylamine hydrochloride salt. The organic layer was dried over anhydrous magnesium sulfate, filtered, and the bulk of the solvent removed under vacuum. On cooling to 0° C., (S)-glycidyl 3-nitrobenzenesulfonate crystallized out of solution. The crystalline derivative (8.2 g; 69% overall yield) was collected by filtration and washed with a small quantity of hexanes. The derivative had a melting point of 57°-59° C. and an optical purity of 96% e.e.

EXAMPLE 4

This example demonstrates the beneficial effect of treating an asymmetric epoxidation reaction mixture with a polyalcohol prior to azeotropic distillation in accordance with the process of the invention.

An epoxidation was carried out with 32 g of allyl alcohol, 7.75 g of L(+)diisopropyl tartrate, 15 g of activated 3A molecular sieves, 250 g of methylene chloride, 7.75 g of titanium isopropoxide, and 208 g of 80% cumene hydroperoxide in cumene. After 14 hours at −15° C., glycidol yield was 70% based on GC analysis. Optical purity of the (S)-glycidol made was 90.9% e.e. as determined by a chiral column GC method.

The reaction mixture was divided into two portions. Into one portion containing 250 g of the epoxidation mixture was added 21 g of propylene glycol (PG:Ti mole ratio=20:1). The sieves were then filtered off. The color of the filtrate was colorless, which is different from the normal yellowish filtrate obtained without the addition of propylene glycol. This suggests that structural modification of the titanium tartrate catalyst had occurred. The methylene chloride was removed under vacuum, followed by the addition of 100 g of cumene for the azeotropic distillation of glycidol. The distillation was carried out using a 20 plate Oldershaw column at 3 mm Hg pressure and a reboiler temperature of 60°-68° C. for 2 hours to obtain a glycidol recovery of 72%, with 9% glycidol in the bottoms and a glycidol loss of 19% by difference. The loss of cumene hydroperoxide as determined by iodometric titration before and after distillation was 9%. The optical purity of the (S)-glycidol recovered in the distillate was determined by the chiral GC method to be 91.0% e.e., indicating no loss in optical purity of the glycidol during the entire work-up procedure.

The other portion of the epoxidation mixture was not treated with propylene glycol. The sieves were filtered off and the methylene chloride was removed under vacuum. After addition of 100 g of cumene, the glycidol was recovered by azeotropic distillation carried out under the above conditions to obtain 75% glycidol recovery with 4% glycidol remaining in the bottoms and a glycidol loss of 20%. The optical purity of the (S)-glycidol recovered in the distillate was only 88.4% e.e., representing a loss of 2.5% e.e. in the optical purity during the work-up. This is attributed to the epoxidation activity of the titanium tartrate catalyst when exposed to higher temperatures in the glycidol recovery process.

TABLE I

| Azeotropic Agent | B.P. at 1013 m bar, °C. | Azeotrope B.P., °C. | P, m bar | glycidol, wt % | glycidol in glycidol-rich phase at 0° C., wt % |
|---|---|---|---|---|---|
| ethyl cyclohexane | 132 | 123 | 1013 | 19.7 | 96.6 |
| n-octane | 126 | 118 | 1013 | 18.0 | 97.0 |
|  |  | 65 | 168 | 9.7 | 97.6 |
|  |  | 48 | 67 | 7.9 |  |
| isooctane | 99 | 96.5 | 1013 | 7.2 | 95.1 |
| n-heptane | 99 | 96.5 | 1013 | 7.9 | 96.8 |
| cumene | 153 | 80 | 133 | 22.5 | 82.0 |
|  |  | 64 | 67 | 21.0 |  |
|  |  | 72 | 87 | 21.0 |  |
| n-hexyl chloride | 133 | 124 | 1013 | 19.0 | 87.6 |
| tetrachloroethylene | 121 | 117 | 1013 | 8.7 | 77.0 |

TABLE II

| Azeotropic Agent | B.P., °C. | P, m bar | Azeotrope B.P., °C. | P, m bar | Glycidol, wt. % |
|---|---|---|---|---|---|
| toluene | 111 | 1013 | 110 | 1013 | 4.9 |
| ethylbenzene | 79 | 165 | 74 | 165 | 13.7 |
|  |  |  | 63 | 87 | 11.0 |
| o-xylene | 81 | 133 | 74 | 133 | 18.0 |
| chlorobenzene | 132 | 1013 | 129 | 1013 | 12.1 |

We claim:

1. A process for recovering an optically active epoxy alcohol from an asymmetric epoxidation reaction mixture comprised of the optically active epoxy alcohol, an organic hydroperoxide, and a transition metal-chiral ligand complex epoxidation catalyst, said process comprising the steps of
(a) contacting the asymmetric epoxidation reaction mixture with
(i) a reducing agent selected from sulfur (II) compounds, sulfur (III) compounds and phosphorus (III) compounds, in an amount effective to reduce the organic hydroperoxide;
(ii) a polyalcohol, in an amount effective to inhibit the epoxidation catalyst; or
(iii) both said reducing agent and said polyalcohol;
(b) conducting a distillation in the presence of an azeotropic agent forming a minimum boiling heterogeneous azeotrope with the epoxy alcohol selected from aromatic hydrocarbons, halogenated aliphatic hydrocarbons, and aliphatic hydrocarbons to remove in vapor form from the asymmetric epoxidation reaction mixture an overhead product comprised of the optically active epoxy alcohol and the azeotropic agent;
(c) condensing the overhead product in liquid form whereby the condensed overhead product phase-separates to form an epoxy alcohol-rich phase and an epoxy alcohol-lean phase; and
(d) separating the epoxy alcohol-rich phase from the epoxy alcohol-lean phase.

2. The process of claim 1 wherein the optically active epoxy alcohol is optically active glycidol.

3. The process of claim 1 wherein the transition metal-chiral ligand complex epoxidation catalyst is derived from an optically active tartaric acid diester and a titanium alkoxide.

4. The process of claim 1 wherein step (b) is carried out at a pressure of from 1 to 100 mm Hg such that the temperature of the asymmetric epoxidation reaction mixture does not exceed 110° C.

5. The process of claim 1 wherein said reducing agent is a sulfur (III) compound selected from alkali metal and alkaline earth salts of hydrogen sulfites, sulfites, and disulfites.

6. The process of claim 1 wherein said reducing agent is a phosphorus (III) compound and wherein said phosphorus (III) compound is a trialkyl phosphite.

7. The process of claim 1 wherein said polyalcohol is a 1,2-diol.

8. The process of claim 1 wherein the azeotropic agent is an aromatic hydrocarbon and said aromatic hydrocarbon is cumene.

9. The process of claim 1 wherein the azeotropic agent is an aliphatic hydrocarbon selected from ethylcyclohexane, n-octane, isooctane, and n-heptane.

10. The process of claim 1 wherein after step (d) the epoxy alcohol-rich phase is subjected to distillation under vacuum so as to remove azeotropic agent.

11. The process of claim 1 wherein the overhead product is condensed in liquid form in step (c) at a temperature of −20° C. to 40° C.

12. The process of claim 1 wherein after step (d) the epoxy alcohol-rich phase is contacted with an organic sulfonyl halide for a time and at a temperature effective to form an organic sulfonate derivative of the epoxy alcohol.

13. A process for recovering optically active glycidol from an asymmetric epoxidation reaction mixture comprised of the optically active glycidol, cumene hydroperoxide, a titanium-chiral tartaric acid diester complex epoxidation catalyst, and allyl alcohol, said process comprising the steps of
(a) contacting the asymmetric epoxidation reaction mixture with
(i) an amount of a reducing agent selected from alkali metal bisulfites, alkali metal sulfites, and trialkyl phosphites at least equivalent on a molar basis to the amount of cumene hydroperoxide to reduce the cumene hydroperoxide;
(ii) an amount of a 1,2-diol at least equivalent on a molar basis to the amount of titanium-chiral tartaric acid diester complex epoxidation catalyst to inhibit said epoxidation catalyst; or
(iii) both said reducing agent and said 1,2-diol, each in an amount at least equivalent on a molar basis to the amount of cumene hydroperoxide and titanium-chiral tartaric acid diester complex epoxidation catalyst respectively to reduce the cumene hydroperoxide and inhibit the epoxidation catalyst;
(b) conducting a distillation in the presence of an azeotropic agent forming a minimum boiling heterogeneous azeotrope with glycidol selected from cumene, hexyl chloride, tetrachloroethylene, n-octane, isooctane, ethyl cyclohexane, and n-heptane to sequentially remove in vapor form from the asymmetric epoxidation reaction mixture a first overhead product comprised of allyl alcohol and a second overhead product comprised of the optically active glycidol and the azeotropic agent;
(c) condensing the second overhead product in liquid form at a temperature of from −20° C. to 40° C. whereby the condensed second overhead product phase-separates to form a glycidol-rich phase and a glycidol-lean phase; and
(d) separating the glycidol-rich phase from the glycidol-lean phase.

14. The process of claim 13 wherein after step (d) the glycidol-rich phase is subjected to distillation under vacuum so as to remove azeotropic agent.

15. The process of claim 13 wherein after step (d) the glycidol-rich phase is contacted with an aromatic sulfonyl halide for a time and at a temperature effective to form an aromatic sulfonate derivative of the glycidol.

16. A process for preparing an organic sulfonate derivative of an optically active epoxy alcohol from an asymmetric epoxidation reaction mixture comprised of the optically active epoxy alcohol, an organic hydroperoxide, and a transition metal-chiral ligand complex epoxidation catalyst, said process comprising the steps of
(a) contacting the asymmetric epoxidation reaction mixture with
(i) a reducing agent selected from sulfur (II) compounds, sulfur (III) compounds, and phosphorus (III) compounds, in an amount effective to reduce the organic hydroperoxide;
(ii) a polyalcohol, in an amount effective to inhibit the epoxidation catalyst; or
(iii) both said reducing agent and said polyalcohol;
(b) conducting a distillation in the presence of an aromatic hydrocarbon azeotropic agent forming a minimum boiling homogeneous azeotrope with the epoxy alcohol to remove in vapor form from the asymmetric epoxidation reaction mixture an overhead product comprised of the optically active epoxy alcohol and the azeotropic agent;
(c) condensing the overhead product in liquid form;

(d) contacting the condensed overhead product with an organic sulfonyl halide for a time and at a temperature effective to form the organic sulfonate derivative of the epoxy alcohol.

17. The process of claim 16 wherein the azeotropic agent is selected from toluene, ethylbenzene, o-xylene, and chlorobenzene.

18. The process of claim 16 wherein the organic sulfonyl halide has the general structure $RSO_2Cl$ wherein R is alkyl, aryl, or aryl alkyl.

19. The process of claim 16 wherein the organic sulfonate derviative is recovered from the condensed overhead product by crystallization.

20. A process for obtaining an aromatic sulfonate derivative of an optically active epoxy alcohol, said process comprising the steps of
    (a) contacting an asymmetric epoxidation reaction mixture comprised of the optically active epoxy alcohol, an organic hydroperoxide, and a transition metal-chiral ligand complex epoxidation catalyst, with
        (i) a reducing agent selected from sulfur (II) compounds, sulfur (III) compounds and phosphorus (III) compounds, in an amount effective to reduce the organic hydroperoxide;
        (ii) a polyalcohol, in an amount effective to inhibit the epoxidation catalyst; or
        (iii) both said reducing agent and said polyalcohol;
    (b) conducting a distillation in the presence of an azeotropic agent forming a minimum boiling heterogeneous azeotrope with the epoxy alcohol selected from aromatic hydrocarbons, halogenated aliphatic hydrocarbons, and aliphatic hydrocarbons to remove in vapor form from the asymmetric epoxidation reaction mixture an overhead product comprised of the optically active epoxy alcohol and the azeotropic agent;
    (c) condensing the overhead product in liquid form whereby the condensed overhead product phase-separates to form an epoxy alcohol-rich phase and an epoxy alcohol-lean phase; and
    (d) contacting the condensed overhead product with an organic sulfonyl halide for a time and at a temperature effective to form the organic sulfonate derivative of the epoxy alcohol.

21. A process for obtaining an aromatic sulfonate derivative of an optically active glycidol said process comprising the steps of
    (a) contacting an asymmetric epoxidation reaction mixture comprised of the optically active glycidol, cumene hydroperoxide, a titanium-chiral tartaric acid diester complex epoxidation catalyst, and allyl alcohol, with
        (i) an amount of a reducing agent selected from alkali metal bisulfites, alkali metal sulfites, and trialkyl phosphites at least equivalent on a molar basis to the amount of cumene hydroperoxide to reduce the cumene hydroperoxide;
        (ii) an amount of a 1,2-diol at least equivalent on a molar basis to the amount of titanium-chiral tartaric acid diester complex epoxidation catalyst to inhibit said epoxidation catalyst; or
        (iii) both said reducing agent and said 1,2-diol, each in an amount at least equivalent on a molar basis to the amount of cumene hydroperoxide and titanium-chiral tartaric acid diester complex epoxidation catalyst respectively to reduce the cumene hydroperoxide and inhibit the epoxidation catalyst;
    (b) conducting a distillation in the presence of an azeotropic agent forming a minimum boiling heterogeneous azeotrope with glycidol selected from cumene, hexyl chloride, tetrachloroethylene, n-octane, isooctane, ethyl cyclohexane, and n-heptane to sequentially remove in vapor form from the asymmetric epoxidation reaction mixture a first overhead product comprised of allyl alcohol and a second overhead product comprised of the optically active glycidol and the azeotropic agent;
    (c) condensing the second overhead product in liquid form at a temperature of from $-20°$ C. to $40°$ C. whereby the condensed second overhead product phase-separates to form a glycidol-rich phase and a glycidol-lead phase; and
    (d) contacting the condensed overhead product with an aromatic sulfonyl halide for a time and at a temperature effective to form the aromatic sulfonate derivative of the glycidol.

* * * * *